United States Patent
Stepina et al.

(10) Patent No.: US 11,751,825 B2
(45) Date of Patent: Sep. 12, 2023

(54) DEVICES, SYSTEMS, AND METHODS FOR CONTROLLING ACQUISITION PARAMETERS WHEN CARRYING OUT A MEDICAL X-RAY EXAMINATION

(71) Applicant: Siemens Healthcare GmbH, Erlangen (DE)

(72) Inventors: Elizaveta Stepina, Adelsdorf (DE); Robert Brauweiler, Baiersdorf (DE); Philip Mewes, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 567 days.

(21) Appl. No.: 16/828,223

(22) Filed: Mar. 24, 2020

(65) Prior Publication Data
US 2020/0305815 A1    Oct. 1, 2020

(30) Foreign Application Priority Data
Mar. 27, 2019   (DE) .......................... 102019204287.2

(51) Int. Cl.
*A61B 6/00*    (2006.01)

(52) U.S. Cl.
CPC ................ *A61B 6/467* (2013.01); *A61B 6/54* (2013.01); *A61B 6/542* (2013.01)

(58) Field of Classification Search
None
See application file for complete search history.

(56) References Cited

U.S. PATENT DOCUMENTS

| | | | |
|---|---|---|---|
| 5,091,656 A | 2/1992 | Gahn | |
| 5,812,050 A * | 9/1998 | Figgins | ................ B60K 26/021 340/407.1 |

(Continued)

FOREIGN PATENT DOCUMENTS

| | | |
|---|---|---|
| CN | 108132274 A | 6/2018 |
| CN | 110610529 A | 12/2019 |

(Continued)

OTHER PUBLICATIONS

"MFS Microscope SW2.4LE-MED", Steute, https://www.steute.de/de/meditec/produkte/medizinische-funk-fussschalter/mfs-microscope-sw24le-med.html, 2019. pp. 1-4.

(Continued)

*Primary Examiner* — Colin T. Sakamoto
(74) *Attorney, Agent, or Firm* — Lempia Summerfield Katz LLC

(57) ABSTRACT

The disclosure relates to devices, systems, and methods for controlling acquisition parameters when carrying out a medical x-ray examination, wherein the device includes a lever. The lever includes a deflectably supported lever arm, which is embodied to be deflected from a rest position to a first end point, in particular a kick-down stop point, and to a second end point, by a force, in particular the force of a foot and/or the force of a hand, wherein a first value of at least one acquisition parameter of the medical x-ray examination is determined by the deflection, wherein the first value is dependent on a measure of deflection of the deflection of the lever arm from the rest position to the first end point, wherein a second value of at least one acquisition parameter of the medical x-ray examination is able to be determined by a deflection of the lever arm to the second end point, and wherein the second value is independent of the (Continued)

measure of deflection of the deflection of the lever arm from the rest position.

23 Claims, 11 Drawing Sheets

(56) References Cited

U.S. PATENT DOCUMENTS

| | | | | |
|---|---|---|---|---|
| 5,934,152 | A * | 8/1999 | Aschoff | B60K 26/02 701/1 |
| 6,070,490 | A * | 6/2000 | Aschoff | F02D 11/02 74/513 |
| 6,179,829 | B1 | 1/2001 | Bisch | |
| 6,666,106 | B1 * | 12/2003 | Hueges | F16H 59/20 74/513 |
| 7,809,111 | B2 * | 10/2010 | Meer | A61B 6/502 378/114 |
| 8,850,640 | B2 * | 10/2014 | Buettner | A61B 6/0487 5/601 |
| 9,892,233 | B2 * | 2/2018 | Zeilinger | A61B 5/0046 |
| 2002/0002873 | A1 * | 1/2002 | Yaddehige | G05G 5/03 74/512 |
| 2003/0190996 | A1 * | 10/2003 | Yone | F02D 11/105 477/120 |
| 2007/0043339 | A1 | 2/2007 | Horvath | |
| 2013/0044859 | A1 | 2/2013 | Yabugami | |
| 2013/0091977 | A1 * | 4/2013 | Fukushima | G05G 1/44 74/513 |
| 2013/0305873 | A1 * | 11/2013 | Cizek | G05G 1/42 74/512 |
| 2015/0145514 | A1 | 5/2015 | Sharma et al. | |
| 2018/0271472 | A1 | 9/2018 | Ercan | |
| 2018/0280099 | A1 * | 10/2018 | Cone | B25J 13/04 |
| 2020/0393951 | A1 | 12/2020 | Schweizer | |
| 2021/0018583 | A1 | 1/2021 | Gui et al. | |
| 2021/0073993 | A1 | 3/2021 | Regensburger et al. | |
| 2021/0088605 | A1 | 3/2021 | Shi | |
| 2021/0270917 | A1 | 9/2021 | Scheffler et al. | |
| 2021/0341436 | A1 | 11/2021 | Perdios et al. | |
| 2021/0356547 | A1 | 11/2021 | Nielsen et al. | |

FOREIGN PATENT DOCUMENTS

| | | | |
|---|---|---|---|
| CN | 112085153 A | 12/2020 | |
| CN | 112470021 A | 3/2021 | |
| CN | 112488289 A | 3/2021 | |
| CN | 112771374 A | 5/2021 | |
| CN | 112912749 A | 6/2021 | |
| CN | 113406544 A | 9/2021 | |
| CN | 114119791 A | 3/2022 | |
| DE | 19801152 A1 | 7/1999 | |
| EP | 1233320 B1 | 8/2006 | |
| JP | H02123099 A | 5/1990 | |
| WO | WO-0005093 A1 * | 2/2000 | ......... B60K 26/021 |

OTHER PUBLICATIONS

A. Bauer: "What is a Car Kickdown?—Explanation", https://uni-24.de/was-ist-ein-kickdown-beim-auto-erklaerung-tz14/, 2019.
German Office Action for German Application No. 10 2019 204 287.2 dated Mar. 2, 2020.
Ashburner, John, and Kari J. Friston. "Unified segmentation." Neuroimage 26.3 (2005): 839-851.
Dai, Xianjin, et al. "Intensity non-uniformity correction in MR imaging using residual cycle generative adversarial network." Physics in Medicine & Biology 65.21 (2020): 215025.
Funai, Amanda K., et al. "Regularized field map estimation in MRI." IEEE transactions on medical imaging 27.10 (2008): 1484-1494.
Tustison, Nicholas J., et al. "N4ITK: improved N3 bias correction." IEEE transactions on medical imaging 29.6 (2010): 1310-1320.

* cited by examiner

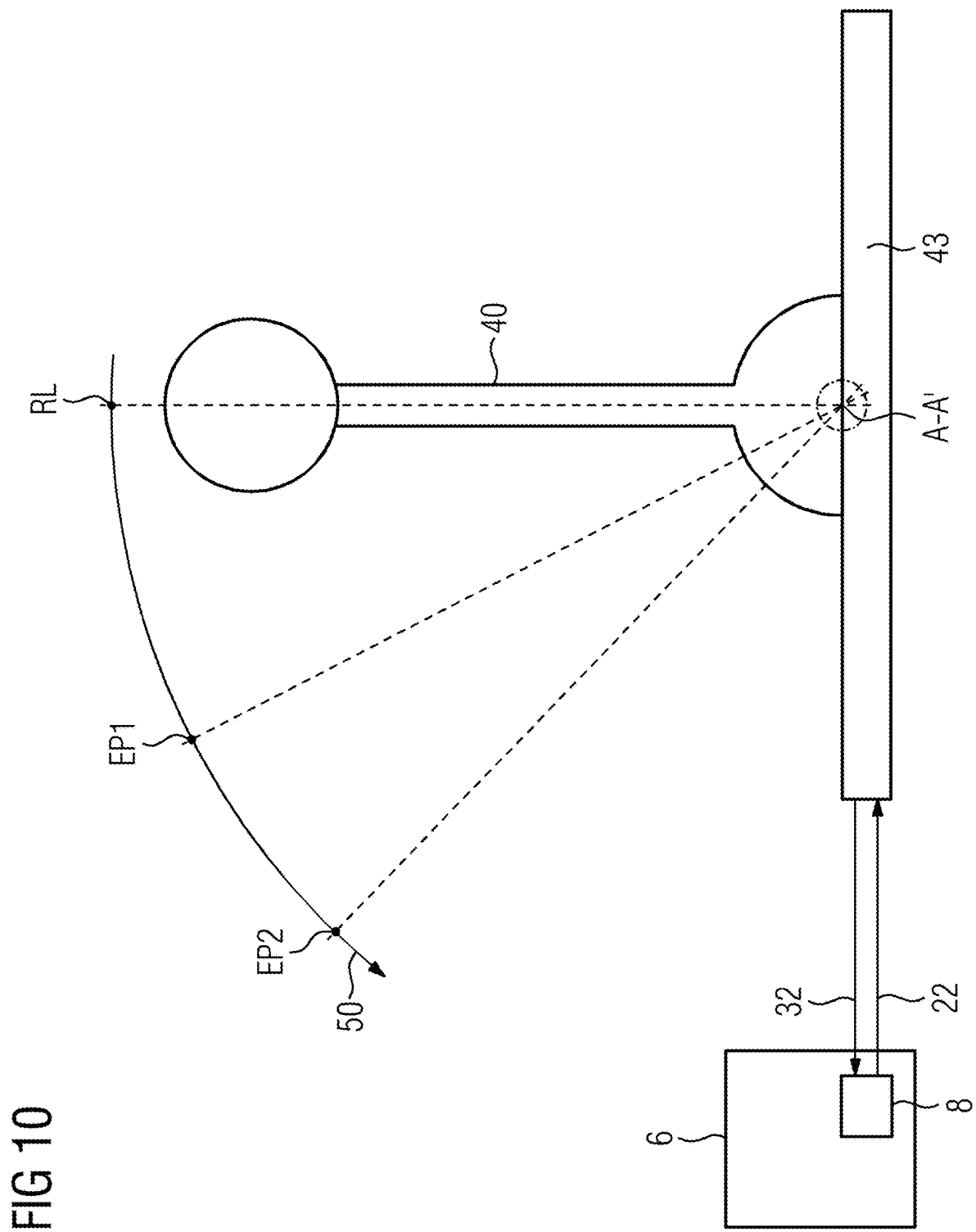

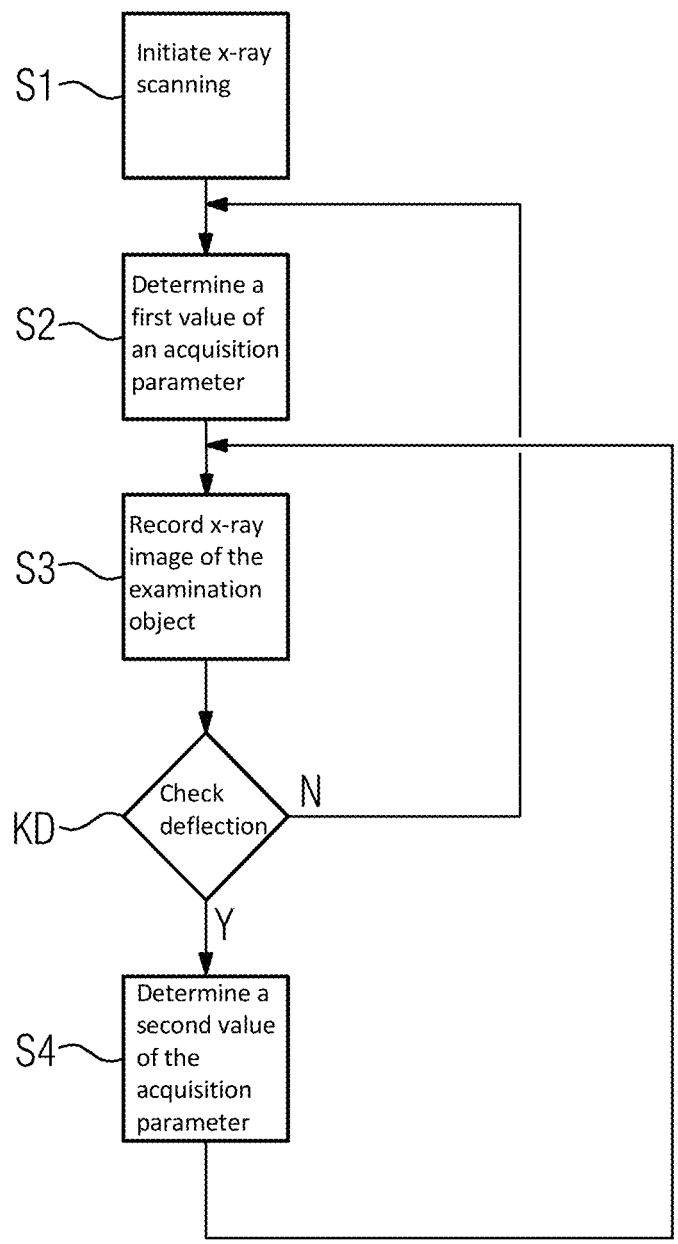

DEVICES, SYSTEMS, AND METHODS FOR CONTROLLING ACQUISITION PARAMETERS WHEN CARRYING OUT A MEDICAL X-RAY EXAMINATION

The present patent document claims the benefit of German Patent Application No. 10 2019 204 287.2, filed Mar. 27, 2019, which is hereby incorporated by reference.

TECHNICAL FIELD

The disclosure relates to devices, systems, and methods for controlling acquisition parameters when carrying out a medical x-ray examination.

BACKGROUND

It is known from the prior art that foot switches are frequently employed, in particular for an intra-operative operation of medical x-ray apparatuses or devices. To date, a split operation of the medical x-ray examination by using an operator's hand and foot for operation, in particular during a surgical intervention, has been necessary. For example, an acquisition protocol may be selected by hand at an input console, in particular a capacitive touch display and/or a keyboard and/or by a hand switch.

Frequently, at least one value of an acquisition parameter may be configured as a function of an imaging objective and/or of the examination object. This may be done in particular by an operator input before or during the medical x-ray examination using a staggered input at the input console.

A combined controlling of acquisition parameters is further known from the prior art via an operator undertaking inputs with their hand and foot. Undertaking inputs by foot here is frequently restricted to a binary foot switch, which is embodied to start and to end the medical x-ray examination on the basis of the acquisition parameters previously selected by inputting them by hand.

Furthermore, a lever may be used, in particular for continuous controlling of an acquisition parameter, by input by an operator's foot.

The disadvantage of the methods known from the prior art is that when the imaging objective is altered and/or more than one acquisition parameter is changed, in particular during the medical x-ray examination, a new input by hand is required. This is a disadvantage in particular at the intra-operative stage. Furthermore, blind operation is frequently not possible, because the setting made has to be checked by the operator. SUMMARY AND DESCRIPTION The underlying object of the disclosure is to specify devices, systems, and methods that make possible an intuitive controlling of at least two acquisition parameters when a medical x-ray examination is being carried out by a blind input of an operator.

The scope of the present disclosure is defined solely by the appended claims and is not affected to any degree by the statements within this summary. The present embodiments may obviate one or more of the drawbacks or limitations in the related art.

Accordingly, a device is proposed that includes a lever, wherein the lever has a deflectably supported lever arm. The lever arm is embodied to be deflected from a rest position to a first end point, in particular a kick-down stop point, and to a second end point by a force, in particular the force of a foot and/or of a hand. Furthermore, a first value of at least one acquisition parameter of the medical x-ray examination is able to be determined as a function of a measure of deflection of the deflection of the lever arm from the rest position to the first end point. A second value of at least one acquisition parameter of the medical x-ray examination is further able to be determined by a deflection of the lever arm to the second end point. Here, the second value is independent of the measure of deflection of the deflection of the lever arm from its rest position.

In particular, the proposed device may be embodied to determine the first and/or the second value, by a sensor unit for example.

The lever arm may include a support surface for a foot and/or hand of an operator. The lever arm is further able to be deflected in such a way that a return to a rest position may take place of its own accord without any force being applied to the lever arm. This may be achieved in particular by mechanical springing and/or a magnetic movement device. In other words, the rest position represents a position of equilibrium of the lever arm in relation to at least one deflection direction, in which the lever arm finds itself without the effect of any force from outside the lever.

The lever may be embodied as a foot pedal for an input by an operator's foot. The lever may further be embodied as a joystick and/or rotary switch for an input by an operator's hand.

The device may have a locking unit, which may fix the lever arm in the rest position, through which a deflection by an operator may be prevented under certain conditions. For example, such a condition may include selection of a first acquisition protocol and/or an acquisition of input data of an examination object. Here, the lever arm may be fixed by the locking unit in the rest position until such time as the condition is fulfilled. After the selection of a first acquisition protocol and/or the acquisition of input data of an examination object, the lever arm is advantageously released for a deflection from its rest position by the locking unit.

By a deflection of the lever arm from the rest position to the first end point, a first value of at least one acquisition parameter of the medical x-ray examination is determined. In particular, an acquisition parameter may include an x-ray tube current and/or a collimator element parameter and/or a collimation parameter and/or an x-ray dose and/or a pulse rate. Furthermore, it is possible to combine a number of acquisition parameters especially advantageously, wherein by a deflection of the lever arm from the rest position to the first end point a determination, (e.g., continuous determination), of a value of the combined acquisition parameters may be made possible. In particular, the advantageous combination of a number of acquisition parameters of which the value may be determined by a deflection of the lever arm may be done as a function of the acquisition protocol selected at the time.

The fact that the first end point has been reached by a deflection of the lever arm by a force may be rendered detectable by an operator, in particular by haptic and/or acoustic and/or optical feedback.

The deflection of the lever arm from the rest position to the first end point may be measured by a measure of deflection. The measure of deflection may include a deflection angle and/or a radian measure and/or a deflection path. In particular, the measure of deflection of the deflection of the lever arm from the rest position may be detected by a sensor unit. Advantageously, the sensor unit is embodied to detect a deflection direction and a measure of deflection of the lever arm from the rest position.

Through a determination of the first value of at least one acquisition parameter as a function of the measure of deflection, the determination of the first value may advantageously include a mapping dependent on the acquisition protocol. Through this, for example, a logarithmic determination and/or a determination classified into different subareas of the value of at least one acquisition parameter may be mapped onto the measure of deflection of the deflection of the lever arm.

A second value of at least one acquisition parameter of the medical x-ray examination may further be determined by a deflection of the lever arm to the second end point. In particular, this may include a change in the first value of at least one acquisition parameter. The fact that the second value is independent of the measure of deflection of the deflection of the lever arm from the rest position to the second end point makes a direct switchover possible. This switchover makes it possible for an operator to select the second value of the at least one acquisition parameter especially intuitively. This may be done either directly from the rest position or starting from a deflection between the rest position and the first end point by a deflection of the lever arm to the second end point.

The second value of the at least one acquisition parameter may especially advantageously be kept in the acquisition protocol. The second value may include a combination of a number of acquisition parameters, which make an optimum image quality possible for the acquisition protocol selected at the time. The second value may include an optimum value of an x-ray tube current and/or a collimator element parameter and/or a collimation parameter and/or an x-ray dose and/or a pulse rate for the acquisition protocol selected at the time.

The fact that the lever arm is supported so that it may be deflected from the rest position to two end points means that an, in particular intuitive, controlling of a number of acquisition parameters by a single input of an operator is made possible. A safe and ergonomic footing of the operator even during the actuation of the lever remains guaranteed by this when using their foot for input for example. Furthermore, the deflection of the lever arm to the second end position directly enables an optimum value, in particular kept in the acquisition protocol, of at least one acquisition parameter to be selected.

In a further advantageous form of embodiment, the second end point is able to be reached in a same deflection direction of the lever arm from the rest position as the first end point. Here, the second end point is arranged in the deflection direction of the lever arm positioned downstream from the first end point. In other words, the second end point may be reached by a deflection of the lever arm from the rest position beyond the first end point. This is advantageous in particular for a simple input by the operator.

In a further advantageous form of embodiment, the first end point may have a threshold, in particular a force threshold, which may be overcome by a force. Here, the second end point is able to be reached after the threshold has been overcome by a deflection of the lever arm, wherein the second end point is embodied as a stop point. In other words, the first end point is embodied as a kick-down stop point, whereby the force threshold arranged there may be overcome by a force, in particular the force of a foot and/or hand. Advantageously, this force is different from the deflection force that is needed for deflection of the lever arm to the first end point.

Furthermore, the second end point is embodied as a stop point, whereby the point cannot be overcome even when maximum force is applied to the lever arm by an operator, for example, by pushing the lever arm as hard as possible.

In particular, there may be haptic feedback to the operator on reaching the first end point by the force threshold to be overcome. In particular, this may make possible a blind and thus especially intuitive deflection of the lever arm from the rest position to the second end point by the operator. Furthermore, incorrect operation of the proposed device may advantageously be excluded by embodying the second end point as a stop point. When maximum force is applied to the lever arm by an operator the maximum point that may be reached here is the second end point.

In a further advantageous form of embodiment, the second end point is able to be reached in a different deflection direction of the lever arm from the rest position to the first end point, wherein the second end point is arranged in the other deflection direction of the lever arm. An example of an embodiment may include a rocker device here, wherein the lever arm is able to be deflected in a rocking motion supported about a rest position. In particular, the rest position may be formed by a horizontal alignment of the lever arm. This form of embodiment makes possible a decoupled determination of the first and second value of at least one acquisition parameter by arranging the second end point in the other deflection direction. The first and the second end point may be embodied here as stop points and are also not able to be overcome by an operator applying the maximum force.

In a further advantageous form of embodiment, the device has at least one switch, wherein the at least one switch is arranged in such a way that the switch is able to be reached during the deflection of the lever arm by a foot of an operator deflecting the lever arm and/or a hand of an operator deflecting the lever arm. A further value of at least one acquisition parameter of the medical x-ray examination is further able to be determined by an actuation of the at least one switch. In particular, the at least one switch may be arranged to the side relative to the deflection direction of the lever arm. This may make a simultaneous deflection of the lever arm and actuation of the at least one switch by the deflecting foot and/or the deflecting hand of the operator possible. This is especially advantageous for controlling a number of acquisition parameters via a single input with the operator's hand or foot while a medical x-ray examination is being carried out.

Through the especially advantageous arrangement of the at least one switch on the lever, the acquisition of at least one further acquisition parameter by a single input with the operator's hand or foot is made possible. In particular, the further value of the at least one acquisition parameter may be at least partly different from the first and the second value. Furthermore, an actuation of the at least one switch may define an operating parameter of the medical x-ray apparatus and/or of a further component, for example, of a peripheral device and/or a surgical instrument.

In a further advantageous form of embodiment, the lever arm has a turntable unit, which is arranged on the lever arm and includes a turntable. The turntable unit is embodied here to make possible a rotational movement of the turntable about an axis at right angles to a support surface of the lever arm. This form of embodiment is especially advantageous for embodying the lever as a foot pedal.

The rotatably supported turntable, which is arranged on the lever arm, advantageously makes possible a lateral movement of an operator's foot that is deflecting the lever arm. This may be of advantage depending on the arrangement of the examination object and/or intra-operative circumstances, where a simultaneous deflection of the lever arm and sideways movement of the operator is necessary.

The turntable unit thus makes possible an especially ergonomic operation of the lever by the operator. If the lever further has at least one switch, the turntable unit may thus make possible an especially simple and ergonomic rotational movement of the operator's deflecting foot to actuate the at least one switch.

In a further advantageous form of embodiment, the turntable unit includes at least one sensor, which is embodied to detect a rotational movement of the turntable, wherein a further value of at least one acquisition parameter of the medical x-ray examination is able to be determined, in particular dependent on a deflection direction of the turntable. In other words, a further value of at least one acquisition parameter may be determined by a rotation of the deflecting foot or the hand of an operator deflecting the lever arm by the turntable unit.

The fact that the further value may be determined as a function of the deflection direction of the turntable enables a sequential change of the further value to be made possible for example. In particular, the rotational movement of the turntable may be undertaken at the same time as the deflection of the lever arm from the rest position to the first and/or second end point. This enables an operator in particular to determine at least two values of at least one acquisition parameter simultaneously during the medical x-ray examination via an input with a single foot or a single hand.

The turntable may be arranged on the lever arm in such a way that it may be reached and moved with the contact point of the deflecting foot or the deflecting hand of the operator. For example, with a pressure point on the front area of the operator's foot with simultaneous deflection of the lever arm, a rotational movement of the heel about the pressure point is made possible. Here, the turntable is moved as well by the deflecting foot and thus makes possible a simple determination of the further value of at least one acquisition parameter.

In a further advantageous form of embodiment, the lever arm has a shear plate unit, which is arranged on the lever arm and includes a shear plate. The shear plate unit is embodied here to make possible a shear movement of the shear plate relative to the lever arm. The shear movement of the shear plate may be predetermined here in particular at right angles to the deflection direction of the lever arm. The shear plate unit may make possible a lateral movement of the deflecting foot or the deflecting hand of an operator deflecting the lever arm. This form of embodiment is especially advantageous for an embodiment of the lever as a foot pedal.

Provided the lever has at least one switch, this may be actuated with a shear movement of the operator's deflecting foot or deflecting hand by the deflecting foot or the deflecting hand or indirectly by the shear plate. This actuation may take place at the same time as a deflection of the lever arm from the rest position.

In a further advantageous form of embodiment, the shear plate unit includes at least one sensor, which is embodied to detect a shear movement of the shear plate relative to the lever arm, wherein a further value of at least one acquisition parameter of the medical x-ray examination is able to be determined, in particular dependent on a shear movement direction of the shear plate. The fact that the further value may be determined as a function of the shear movement direction of the shear plate enables a sequential change of the further value to be determined, for example. In particular, the shear movement of the shear plate may occur at the same time as a deflection of the lever arm from the rest position to the first and/or second end point. Advantageously, the shear movement direction is predetermined at right angles to the deflection direction of the lever arm.

In particular, the shear plate unit may be arranged on the lever arm in such a way that it may be reached and moved with the contact point of the deflecting foot of the operator. For example, with a pressure point in the front area of the operator's foot, with a simultaneous deflection of the lever arm a rotational movement of the front of the foot about the heel may be made possible. The shear plate is moved at the same time by the deflecting foot here and thus makes possible a simple determination of the further value of at least one acquisition parameter.

In a further advantageous form of embodiment, the device includes a signal unit, which is embodied to output a signal able to be detected by the operator during a deflection of the lever arm. The signal is determined here by the measure of deflection of the lever arm at the time and/or is able to be triggered by the deflection of the lever arm. For example, an acoustic signal, in particular a click, may give an acknowledgement to an operator on reaching the first and/or second end point. Furthermore, the signal unit may be embodied to output haptic feedback, for example, a vibration and/or a force feedback, to an operator. This may be advantageous in particular with a graduated mapping between the measure of deflection of the deflection of the lever arm from the rest position up to the first end point for the first value of the at least one acquisition parameter. A direct acknowledgement may be given to the operator here when individual deflection stages are reached and/or overcome.

Furthermore, the signal unit may advantageously be embodied to output an optically detectable indication, for example, a light intensity and/or light color, at least as a function of the measure of deflection of the deflection of the lever arm. For example, the signal unit may have one or more LEDs, which may give the operator direct feedback about the deflection of the lever arm and/or about actuation of further switches and/or sensors.

The signal unit may further be embodied to output a warning signal to an operator after a predetermined time has elapsed during which the lever arm was continuously deflected from the rest position. This may be advantageous in particular if an operator unintentionally deflects the lever arm from the rest position. An unnecessary irradiation of the examination object and/or of the operator with x-rays may be prevented by this.

In a further advantageous form of embodiment, the lever arm is deflected about a first axis, wherein the lever arm is supported deflectably about a further axis, in particular a vertical axis, different from the first axis. A deflection of the lever arm about this further axis is restricted here by an end point in each case in each of the further deflection directions. A further value of at least one acquisition parameter of the medical x-ray examination, in particular dependent on a deflection direction of the lever arm about the further axis, may further be able to be determined by a deflection of the lever arm about the further axis from the rest position.

The further axis, different from the first axis, may run at right angles to the first axis. An especially controlled deflection of the lever arm in the number of deflection directions by the deflecting foot or the deflecting hand of the operator is made possible by this. The further axis may be arranged in such a way that there may be a simultaneous deflection of the lever arm about the first and the further axis from the rest position. The rest position here may refer to a position of the lever arm in which the lever arm is located without any force being applied by the operator. Furthermore, the lever arm in particular returns to the rest position of its own accord after a force has finished being applied by the operator. This may be achieved, for example, by mechanical springing in the number of deflection directions of the lever arm.

The one end point in each case in each of the two deflection directions of the lever arm about the further axis may be embodied as a stop point. In particular, the lever arm may be deflected from the rest position about the further axis independently of and/or without a deflection of the lever arm about the first axis. This may be advantageous for example for an, in particular sequential, determination of the acquisition protocol before a medical x-ray examination. Provided the device has a locking unit, the deflection of the lever arm about an individual axis may be locked. For example, before the medical x-ray examination the deflection of the lever arm about the first axis may be locked so that an acquisition protocol may be determined by a deflection of the lever arm about the further axis. During or after the medical x-ray examination the locking unit may release the deflection of the lever arm about the first axis, whereby a determination of the first and the second value of at least one acquisition parameter is made possible.

The device may further be used in the proposed form of embodiment for controlling at least one operating parameter of a movable medical x-ray apparatus. For example to control the movement of an x-ray device during the medical x-ray examination. Advantageously, the controlling of the acquisition parameters in particular at the same time as the controlling of the at least one operating parameter may be done by input by a deflecting foot or a deflecting hand of an operator.

Described below are methods for controlling of acquisition parameters when carrying out a medical x-ray examination. The advantages of the methods correspond to the advantages of the devices for controlling of acquisition parameters when carrying out a medical x-ray examination, which have been explained in detail above. Features, advantages or alternate forms of embodiment mentioned here may likewise be transferred to the other claimed subject matter and vice versa.

In certain methods, the medical x-ray examination is carried out by a medical x-ray apparatus and a lever. The lever here includes a deflectably supported lever arm, which is embodied to be deflected from a rest position to a first end point, (e.g., a kick-down stop point), and to a second end point. In this case, x-ray scanning of the examination object is initiated by a deflection of the lever arm from the rest position. A first value of at least one acquisition parameter of the medical x-ray examination is further determined, wherein the first value is dependent on a measure of deflection of the deflection of the lever arm from the rest position to the first end point. Furthermore, in a deflection of the lever arm to the second end point, a second value of at least one acquisition parameter of the medical x-ray examination is determined, wherein the second value is independent of the measure of deflection of the deflection of the lever arm from the rest position to the second end point.

The fact that the x-ray scanning is initiated by a deflection of the lever arm from the rest position means that it is insured that no autonomous initiation of the x-ray scanning without an input by an operator may take place. The device is embodied in such a way that the lever arm, after each deflection from the rest position, returns again of its own accord to the rest position and remains at rest there without an application of an external force, for example, by an operator.

The lever may further be embodied such that the lever arm, on reaching the rest position, latches into this position in the interim. A deflection of the lever arm from the rest position in this form of embodiment is only possible by overcoming a force threshold, whereby in particular an inadvertent deflection of the lever arm from the rest position by an operator may be avoided.

The first value of at least one acquisition parameter is determined as a function of the measure of deflection of the deflection of the lever arm from the rest position to the first end point. Through this, an operator may control the first value, in particular steplessly or in acts, during the medical x-ray examination.

A mapping specification may be used in particular for the determination of the first value, wherein the mapping specification may include an assignment of the first value to the measure of deflection of the deflection of the lever arm from rest position to the first end point at the time. The mapping specification may further be dependent on the acquisition protocol selected at the time. In other words, a determination of the first value of at least one acquisition parameter depending on the acquisition protocol is made possible by this.

For an especially intuitive and blind controlling of the acquisition parameters an operator, after selecting an acquisition protocol, may deflect the lever arm to the second end point. Through this, the second value of at least one acquisition parameter is determined independently of the measure of deflection of the deflection of the lever arm from the rest position to the second end point. In particular, the second value may be determined on the basis of an optimum value for a specific imaging objective and/or examination object kept in the acquisition protocol. X-ray scanning of the examination object with the second value of at least one acquisition parameter may be initiated here directly by the deflection of the lever arm to the second end point.

Provided the second end point is arranged after the first end point in the same deflection direction of the lever arm from the rest position, a threshold may be arranged at the first end point. By a deflection of the lever arm beyond the first end point and thus beyond the threshold, direct haptic feedback may be given to operators about deflection of the lever arm. This is in particular advantageous for a blind operation, for example, for a medical x-ray examination during a surgical intervention.

In a further advantageous form of embodiment, a graphical representation of the measure of deflection of the deflection of the lever arm at the time may be displayed on a display unit, for example, a monitor and/or a display and/or an LED display and/or a scale. Direct feedback about the deflection of the lever arm at the time to operators is made possible by this. In particular, the display of the deflection at the time may include a graphical representation of the measure of deflection and/or of a deflection direction. Furthermore, a graphical representation of the first and/or second value of the at least one acquisition parameter determined at the time may be displayed on the display unit. A mapping specification may be used here, wherein the mapping specification may include an assignment of the first value to the measure of deflection at the time. The graphical representation of the deflection of the lever arm at the time may further be undertaken as a function of the acquisition protocol selected at the time.

If the proposed device, which has at least one switch, is used in an advantageous form of embodiment, then on actuation of the at least one switch, a further value of at least one acquisition parameter of the medical x-ray examination may be determined. This enables an operator advantageously to determine at least two values of at least one acquisition parameter at the same time with a single deflecting foot or a single deflecting hand.

In a further advantageous form of embodiment, a further value of at least one acquisition parameter of the medical x-ray examination may be determined. This is made possible in particular through the use of a device embodied for this purpose, as is proposed in one of the advantageous forms of embodiment. The further value may be determined here at the same time as a deflection of the lever arm from the rest position and with the same deflecting foot or the same deflecting hand of the operator.

In a further advantageous form of embodiment, the determination of the further value of at least one acquisition parameter of the medical x-ray examination may trigger storage of the first value, in particular in a recording protocol. The further value may be considered here in particular as a trigger for storing the first value. A determination of the further value enables the operator, in particular at the same time as a deflection of the lever arm from the rest position to the first end point, to trigger storage of the first value. The first value may be stored here as an optimum value in a recording protocol. The optimum value now held in the recording protocol may be retrieved by this for a deflection of the lever arm to the second end point and used for the x-ray scanning. This function for the determination of the further value may be considered as a memory function.

For example, a graphical representation of an x-ray image and/or of a scene, which includes a number of recorded x-ray images, (e.g., last recorded by x-ray scanning), may be displayed on a display unit, (e.g., a monitor and/or display). This graphical representation may further be undertaken in combination with a graphical representation of the measure of deflection of the lever arm at the point of recording the respective x-ray image. Advantageously an operator, by looking at the graphical representation, is thus given direct feedback about image quality of the x-ray image and/or about an imaging objective.

In a further advantageous form of embodiment, the determination of the further value of at least one acquisition parameter of the medical x-ray examination makes it possible to switch between different recording protocols of the medical x-ray examination and/or makes possible a selection, in particular sequential selection, of at least one acquisition parameter for the determination of the first value by the deflection of the lever arm from the rest position to the first end point. It is especially advantageous here for the device used to be embodied to determine the further value at least as a function of a further deflection direction of the lever arm and/or a deflection direction of a turntable and/or of a shear movement direction of a shear plate. Through this, a sequential selection of a recording protocol may be made possible for an operator.

In particular, the further value may be assigned as a function of the deflection of the lever arm from the rest position to the first and/or second end point. This means that, for example, there may be a selection of a recording protocol via the further value, unless the lever arm is located in the rest position. No x-ray scanning is initiated here.

If the lever arm is deflected from the rest position to the first and/or second end point by a foot entry of an operator, x-ray scanning is initiated. At the same time, there may be a determination, in particular sequential determination, of an acquisition parameter and/or of an operating parameter, e.g., via the further value. For example, the first value, which is dependent on the measure of deflection of the lever arm, is used to determine an x-ray radiation dose, while the further value may be used to switch between different pulse rates.

Furthermore, at least one operating parameter may be switched over via the further value. For example, during the x-ray scanning another exposure value and/or collimation value may be set via the further value. An operating parameter of a peripheral device, (e.g., of a surgical instrument), may further be determined by the further value.

This makes it possible for a number of acquisition parameters of the medical x-ray examination and/or at least one operating parameter of the medical x-ray device to be controlled by a single deflecting foot or a single deflecting hand of an operator. This is especially advantageous for use in an intra-operative environment, because the operator may check the medical x-ray examination during an intervention with a single foot or a single hand in a blind and especially intuitive manner.

In a further advantageous form of embodiment, an assignment of at least one determination function of the lever to the determination of the first and/or the second and/or the further value of at least one acquisition parameter in each case may be adapted, wherein this adaptation is undertaken as a function of a recording protocol of the medical x-ray examination. It may be advantageous, depending on imaging objective and/or acquisition protocol, to control a value of changed acquisition parameters via the foot entry of an operator. For example, this may make possible controlling of an at least different subset of acquisition parameters for different acquisition protocols. In particular, an assignment dependent on the acquisition protocol may be advantageous for the determination of the further value, because through this acquisition parameters and/or operating parameters configured to the imaging objective may be controlled.

The acquisition protocol may further include assignment information about the determination functions of the lever. Through this, an especially individual adaptation of the assignment of the determination functions of the lever is made possible for an operator. In particular, a user-specific assignment profile may be loaded from a memory unit at the beginning of a medical x-ray examination. This may make possible an especially intuitive operation and user-specific tuning of the operation of the proposed device.

In a further advantageous form of embodiment, (e.g., for a deflection of the lever arm), a signal able to be detected by the operator is output, which is determined by the measure of deflection of the lever arm at the time and/or is triggered by the deflection of the lever arm from the rest position. In other words, a signal detectable for the operator, in particular an acoustic and/or an optical and/or haptic signal, may be output by a signal unit. The signal may be triggered here by a deflection of the lever arm from the rest position and/or be dependent on a measure of deflection of the deflection of the lever arm and/or a deflection direction of the lever arm.

A medical x-ray apparatus with a device is further proposed, which is embodied to carry out a method for controlling of acquisition parameters when a medical x-ray examination is being carried out. In particular the x-ray device is embodied, when the lever arm is deflected from the rest position, to carry out x-ray scanning of the examination object.

Furthermore, a processing unit, (e.g., a microprocessor), is proposed, which is embodied to process information and/or data and/or signals from the device and/or further components. The processing unit is further embodied to send control commands to a medical x-ray apparatus and/or the device and/or further components.

A computer program product is further proposed, which includes a program and is able to be loaded directly into a memory of a programmable arithmetic unit and has program code or functions, e.g., libraries and auxiliary functions, for carrying out a method for controlling of acquisition parameters when a medical x-ray examination is being carried out, when the computer program product is executed. The computer program product in this case may include software with a source code, which still has to be compiled and linked or only has to be interpreted, or executable software code, which only has to be loaded into the processing unit to execute it. The computer program product enables the method for controlling of acquisition parameters when a medical x-ray examination is being carried out to be carried out quickly, identically repeatably and robustly. The computer program product is configured so that it may carry out the method acts by the processing unit. The processing unit includes the appropriate requirements, such as having a corresponding main memory, a corresponding graphics card, or a corresponding logic unit, so that the respective method acts may be carried out efficiently.

The computer program product is stored for example on a computer-readable medium or held on a network or server, from where it may be loaded into the processor of a processing unit, which is directly connected to the processing unit or may be embodied as part of the processing unit. Furthermore, control information of the computer program product may be stored on an electronically-readable data medium. The control information of the electronically-readable data medium may be designed in such a way that it carries out a method when the data medium is used in a processing unit. Examples of electronically-readable data media are a DVD, a magnetic tape or a USB stick, on which electronically-readable control information, in particular software, is stored. When this control information is read from the data medium and stored in a processing unit, all forms of embodiment of the method described above may be carried out. The disclosure may thus also be based on the computer-readable medium and/or the electronically-readable data medium.

BRIEF DESCRIPTION OF THE DRAWINGS

Exemplary embodiments of the disclosure are shown in the figures and will be described in greater detail below. In different figures, the same reference characters are used for the same features. In the figures:

FIG. 10 depicts a schematic diagram of a hand lever kick-down stop point according to an embodiment FIG. 11 depicts a schematic diagram of an example of method acts for controlling of acquisition parameters when a medical x-ray examination is being carried out.

DETAILED DESCRIPTION

Figure 1:
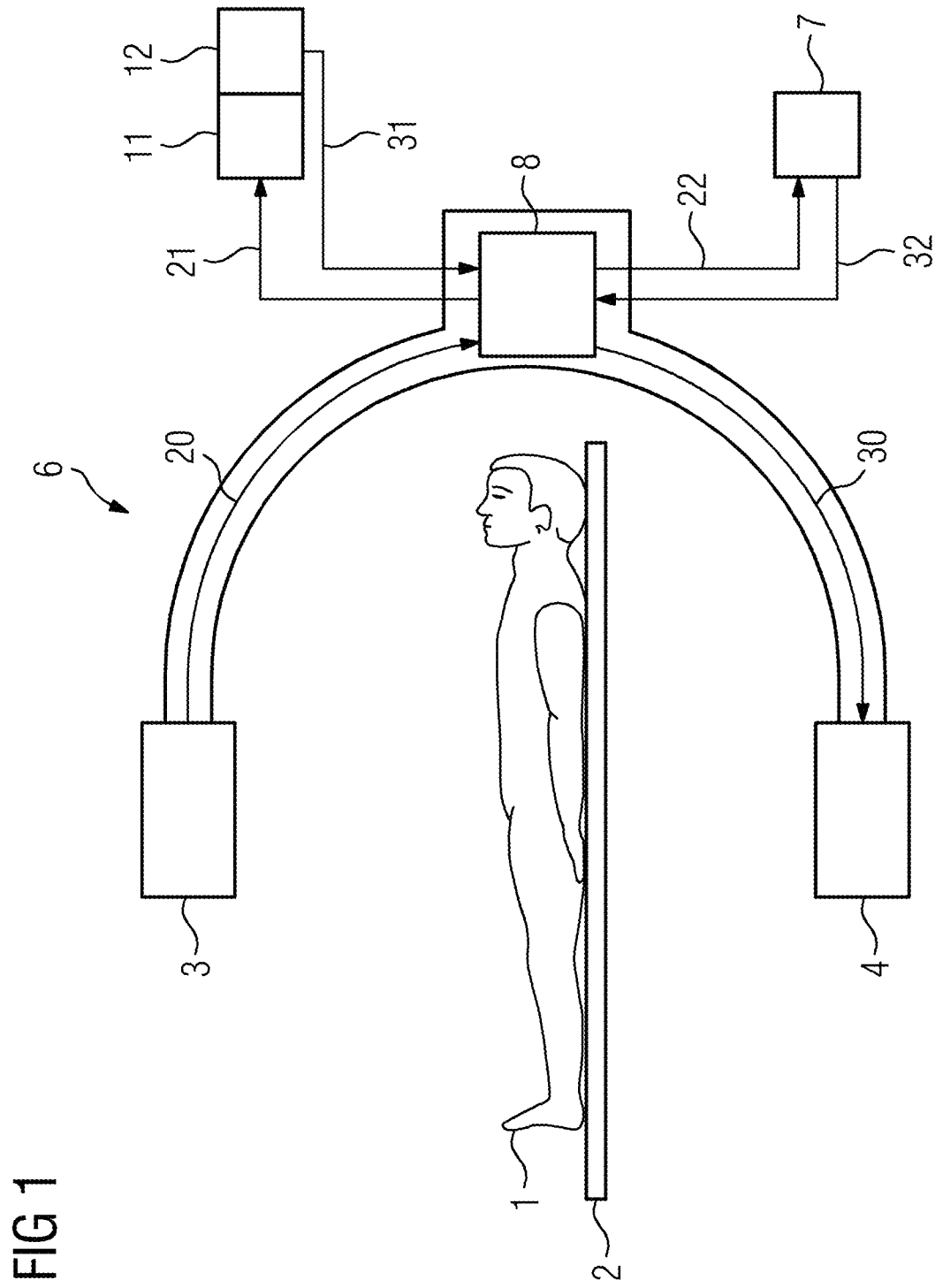
FIG. 1 depicts a schematic diagram of a medical x-ray device according to an embodiment.

FIG. 1 depicts an example of a medical C-arm x-ray device 6. In particular, the medical C-arm x-ray device 6 includes an x-ray unit 4 and a detection unit 3, as well as a processing unit 8. A form of embodiment of the device for controlling of acquisition parameters when a medical x-ray examination is being carried out is shown as lever 7. The lever 7 may include a lever processing unit 43 and a deflectably supported lever arm 40.

When a medical x-ray examination is being carried out at the beginning, there may be an acquisition protocol by an input of an operator via an input unit 12. To do this, the input unit 12 sends a control command 31 to the processing unit 8. A graphical representation of the selected acquisition protocol may further be displayed on a display unit 11. For this, the processing unit 8 may send a control command 21 to the display unit 11. The input unit 12 may be integrated into the display unit 11, for example, with a capacitive input display.

If an operator input at the lever 7 results in a deflection of the lever arm from the rest position, x-ray scanning of an examination object 1 is initiated. When this occurs, the lever processing unit 43 sends a control command 32 to the processing unit 8, which in its turn sends a control command 30 to the x-ray unit 4. X-ray scanning of an examination object 1 may be initiated by this, wherein the examination object 1 may be arranged for this on a patient support unit 2. The detection unit 3 is further embodied, when exposed to x-rays, to detect an x-ray image and to send a corresponding signal 20 to the processing unit. To display a graphical representation of the x-ray image, in particular the last image recorded, on a display unit 11, the processing unit 8 may send a control command 21 to the display unit 11.

Furthermore, on the basis of the control command 32 from the lever processing unit 43, the processing unit 8 may establish a measure of deflection of the deflection of the lever arm from the rest position. A graphical representation of the measure of deflection may be made possible by this by sending the control command 21 to the display unit 11.

Figure 2:
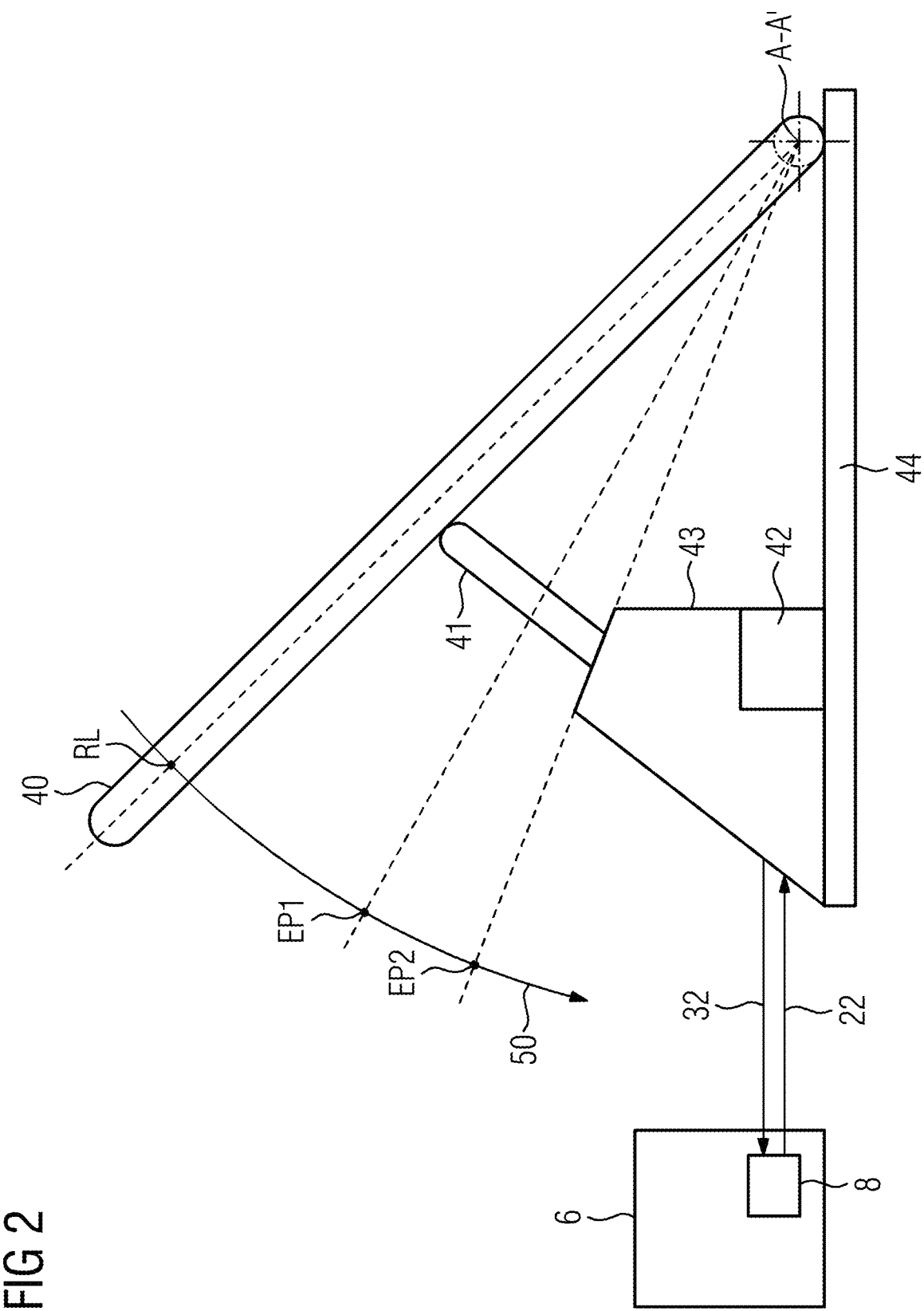
FIG. 2 depicts a schematic diagram of a foot pedal with an electronic and/or electromagnetic kick-down stop point according to an embodiment.

FIG. 2 depicts a schematic diagram of an advantageous form of embodiment of the proposed device, wherein the device includes a foot pedal. The foot pedal here, as an embodiment of the lever, includes a lever arm 40, which is supported deflectably about a first axis A-A'. The lever arm 40 is further fastened deflectably to a base plate 44 of the foot pedal. Without the application of a force by an operator, the lever arm 40 is located in a rest position RL. If a force, in particular the force of a foot, of the operator acts at least partly in the deflection direction 50 of the lever arm 40, the arm is deflected out of its rest position RL. The lever arm here is supported for deflection to a first end point EP1, wherein a second end point EP2 is able to be reached in the same deflection direction 50 of the lever arm 40 from the rest position RL as the first end point EP1. Furthermore, the second end point EP2 is arranged downstream of the first end point EP1.

With a deflection of the lever arm 40 from the rest position RL to a first end point EP1, a first value of at least one acquisition parameter of the medical x-ray examination is determined. In this case, the first value is dependent on a measure of deflection of the deflection of the lever arm 40 from the rest position RL to the first end point EP1. To this end, the foot pedal may have a plunger 41 and a lever processing unit 43.

With a deflection of the lever arm 40 from the rest position RL, the plunger 41 is pressed by the force acting on it into the lever processing unit 43. The lever processing unit 43 may include a sensor unit (not shown), which is embodied to detect a distance covered by the plunger 41 and to send a corresponding signal to the lever processing unit 43. For its part, the lever processing unit 43 may send a control command 32 to the processing unit 8 by the signal from the sensor unit.

The lever processing unit 43 may be embodied to exert a force resistance on the plunger 41, for example by an electromagnetic and/or mechanical springing unit (not shown).

The first end point EP1 is embodied in particular as a kick-down stop point. In this case, a force threshold may be arranged at the first end point EP1, which may be overcome by a force, for example, a force of the operator's foot. After the force threshold has been overcome, the second end point EP2 is able to be reached by a deflection of the lever arm 40. The second end point EP2 is also embodied as a stop point. The stop point at the position of the second end point EP2 may be formed, for example, by a support surface of the lever arm 40 on the lever processing unit 43.

With a deflection of the lever arm 40 beyond the force threshold at the first end point EP1 to the second end point EP2, a control command 32, independent on the measure of deflection of the deflection of the lever arm 40, is sent from the lever processing unit 43 to the processing unit 8. Through this, the processing unit 8 may determine a second value of at least one acquisition parameter. This second value may include an optimum value of at least one acquisition parameter of the medical x-ray examination, which in particular is kept in the acquisition protocol selected at the time.

Furthermore, the foot pedal may include a signal unit 42. The signal unit 42 may be embodied, on a deflection of the lever arm 40, to output a signal detectable for an operator, which is determined by the measure of deflection of the lever arm 40 at the time and/or is able to be triggered by the deflection of the lever arm 40. In particular, the signal unit 42 may be integrated into the lever processing unit 43, whereby the signal able to be detected by the operator may be triggered directly by a movement of the plunger 41.

Figure 3:
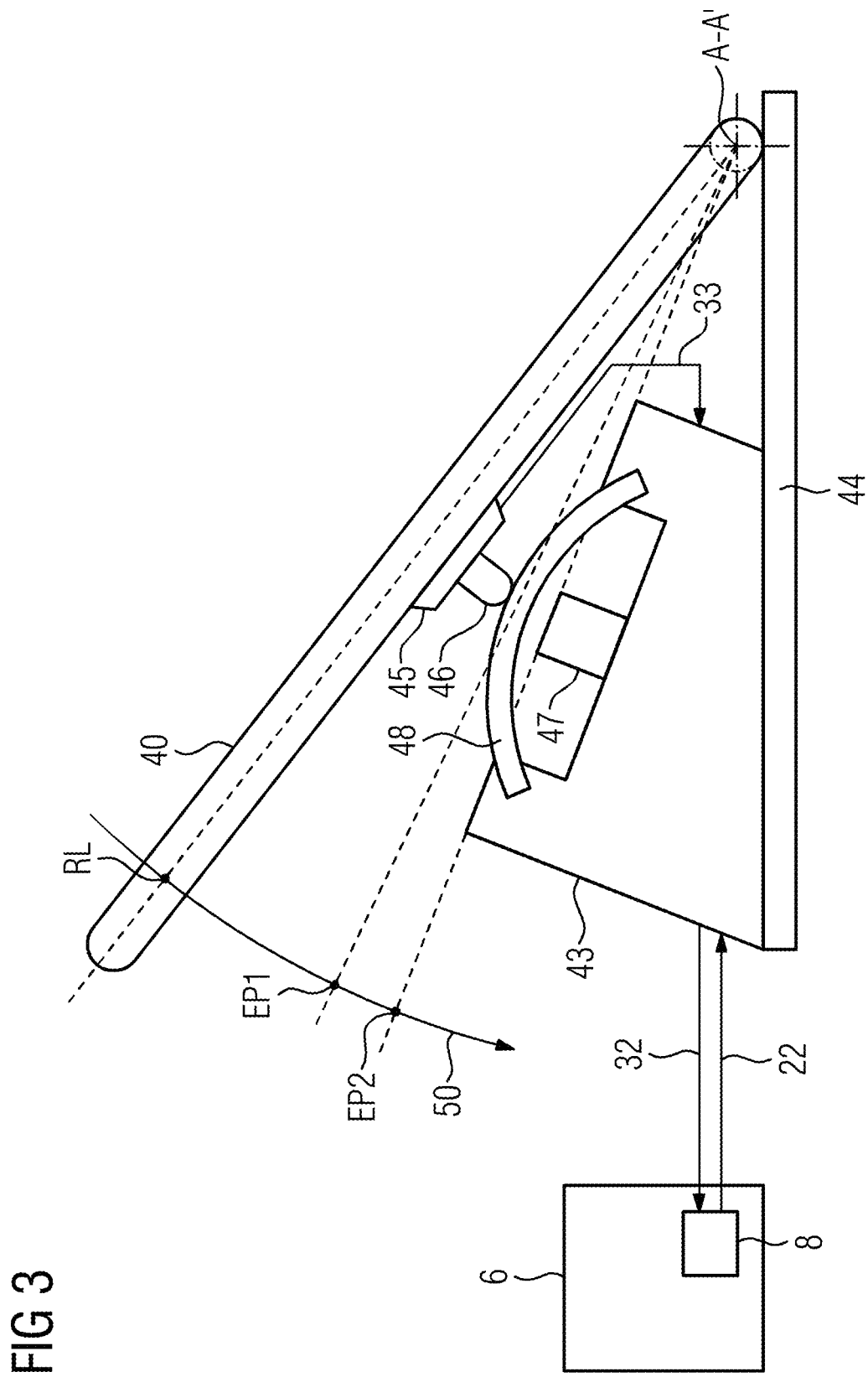
FIG. 3 depicts a schematic diagram of a foot pedal with a mechanical kick-down stop point according to an embodiment.

Depicted in FIG. 3 is a schematic diagram of a foot pedal with mechanical kick-down stop point at the first end point EP1. Here, a piston 46 and a sensor unit 45 are arranged directly on the lever arm 40. With a deflection of the lever arm 40 from the rest position RL to the first end point EP1, the piston 46 is pushed into the sensor unit 46. The piston 46 may also be supported by springs on the lever arm 40 and/or the sensor unit 46. The sensor unit 46 may be embodied to establish a measure for the distance covered by the piston 46 and to send a signal 33 to the lever processing unit 43. Through this, the measure of deflection of the deflection of the lever arm 40 from the rest position RL may be determined.

The form of embodiment shown in FIG. 2 further has a mechanical spring 48 at its first end point EP1, for example, a coil spring and/or a leaf spring. Through this, a force threshold able to be overcome by an operator is obtained at the first end point EP1. In this case, the force necessary to overcome the force threshold is different from the force that is needed for deflection of the lever arm 40 from the rest position RL to the first end point EP1. With a deflection of the lever arm 40 beyond the force threshold, there is a deflection of the spring 48, wherein a switch 47 is actuated. This switch is arranged at the second end point EP2 and makes possible a determination of the second value independent of the measure of deflection of the deflection of the lever arm 40. For this, the switch 47 may be integrated into the lever processing unit 43, which may detect and process the signal 33 from the sensor unit and the signal of the switch 47. Furthermore, the processing unit 43, with a deflection of the lever arm 40 from the rest position RL, depending on the deflection, may send a control command 32 to the processing unit 8 on the basis of the signal 33 and/or of the signal of the switch 47.

Figure 4:
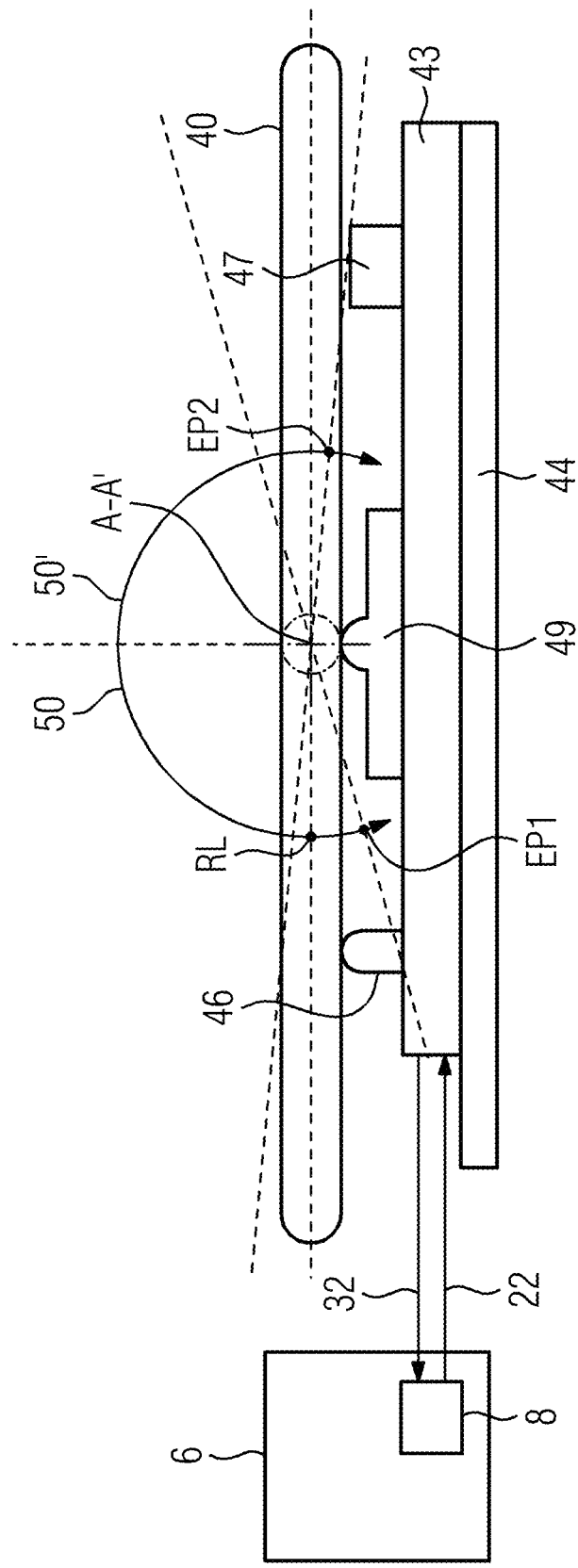
FIG. 4 depicts a schematic diagram of a foot pedal embodied as a rocker device according to an embodiment.

Depicted in FIG. 4 is a schematic diagram of a foot pedal embodied as a rocker device. Here, the second end point EP2 is able to be reached in a different deflection direction 50' of the lever arm 40 from the rest position RL to the first end point EP1. In this case, the second end point EP2 is arranged in the other deflection direction 50' of the lever arm 40. In this form of embodiment, the foot pedal has a support unit 49, which makes possible a rocking movement of the lever arm 40 in the first deflection direction 50 and in the other deflection direction 50' about an axis A-A'. With a deflection of the lever arm 40 from the rest position RL to the first end point EP, a plunger 46 is pushed into the lever processing unit 43. The lever processing unit here includes a sensor unit (not shown), which is embodied to establish a measure of the distance covered by the plunger 46. Arranged in the other deflection direction 50' is the second end point EP2, wherein with a deflection of the lever arm 40 to the second end point EP2, a switch 47 is actuated. The switch may be integrated into the lever processing unit 43.

In this form of embodiment, the first end point EP1 and the second end point EP2 are each embodied as a stop point. This means that the two end points cannot be overcome by a force exerted by an operator. Depending on a signal from the sensor unit to the plunger 46 and a signal from the switch 47, the lever processing unit 43 may be embodied to establish the deflection direction and a measure of deflection of a deflection of the lever arm 40. In this case, the lever processing unit 43 sends a control command 32 to the processing unit 8.

Figure 5:
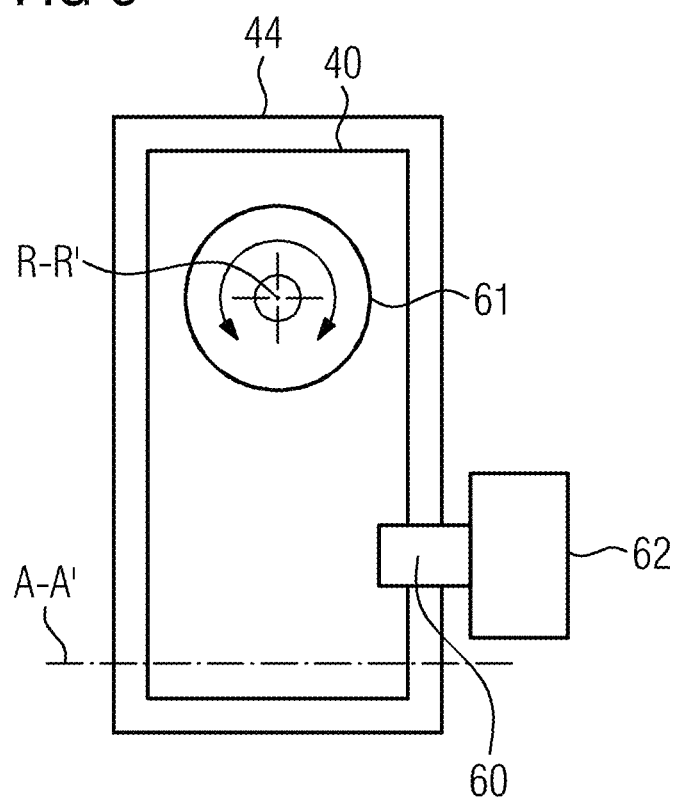
FIG. 5 depicts a schematic diagram of an overhead view of a foot pedal with a turntable unit and a switch according to an embodiment.

Depicted in FIG. 5 is a schematic diagram of an overhead view of a foot pedal with a turntable unit and a switch. The foot pedal has a switch 60. Wherein the switch 60 is arranged at the side of the lever arm 40, whereby the switch 60 is able to be reached with each deflection of the lever arm 40 by an operator's foot deflecting the lever arm. The foot pedal further includes a sensor unit 62, which, on actuation of a switch 60 sends a control command 34 to the lever processing unit 43. The lever processing unit 43 then sends a control command 32 to the processing unit 8, whereby a further value of at least one acquisition parameter of the medical x-ray examination is determined.

So that switch 60 is able to be reached by a deflecting foot of the operator in an especially ergonomic and simple manner, in particular during a deflection of the lever arm 40, the lever arm 40 has a turntable unit 61. The turntable unit 61 is embodied to make possible a rotational movement of the turntable about an axis R-R' at right angles to a support surface of the lever arm 40. An arrangement of the turntable unit 61 at a support point of the deflecting foot of the operator on the support surface of the lever arm 40 means that the deflection of the lever arm 40 about the axis A-A' as well as the actuation of the switch 60 with the deflecting foot are possible at the same time.

Figure 6:
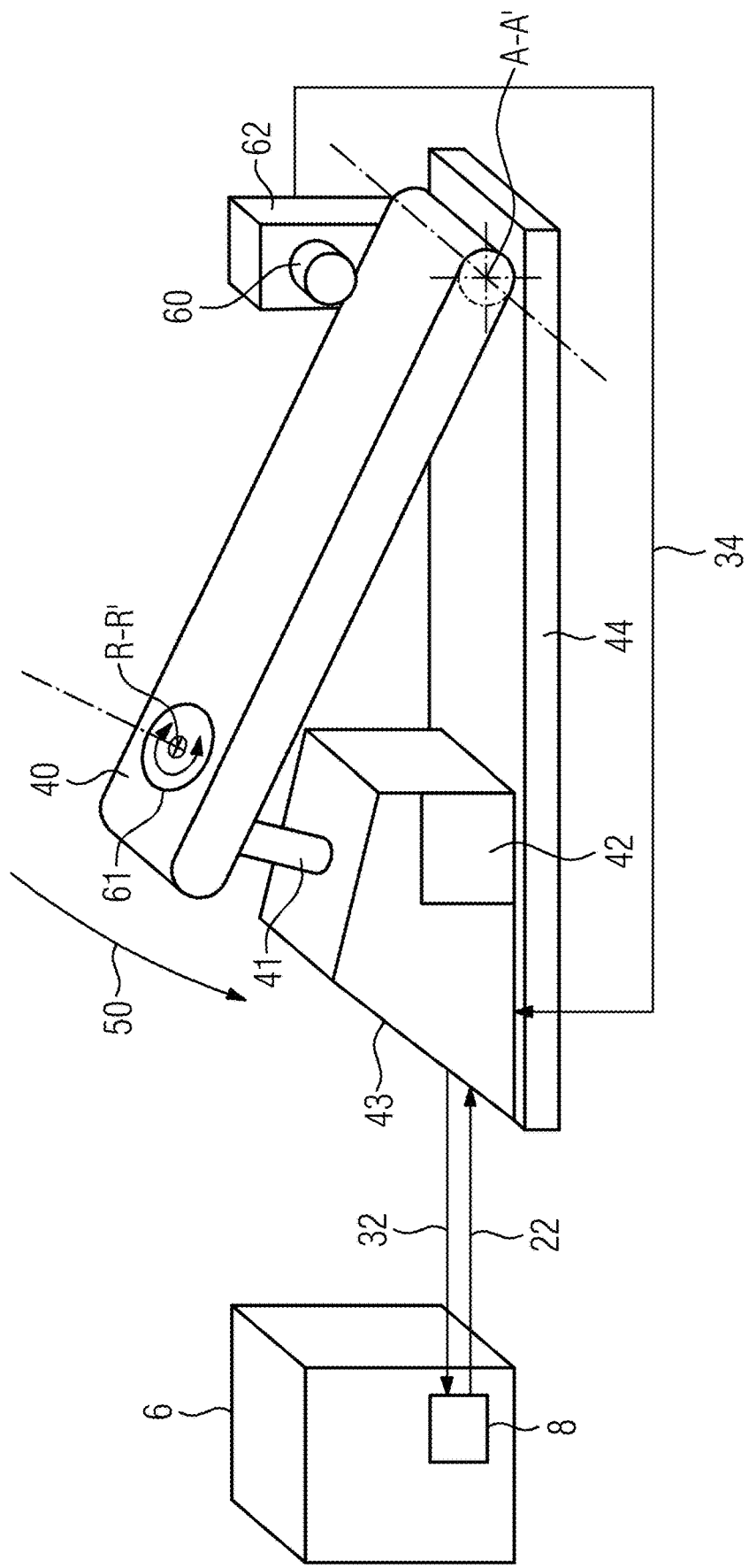
FIG. 6 depicts a schematic diagram of a foot pedal with a turntable unit and a switch according to an embodiment.

Depicted in FIG. 6 is a schematic diagram of a perspective view of a foot pedal with a turntable unit and a switch. The form of embodiment shown here corresponds to the form of embodiment depicted in FIG. 5. Here, the signal unit 42 may be embodied, on actuation of the switch 60, to output a signal able to be detected by an operator.

Figure 7:
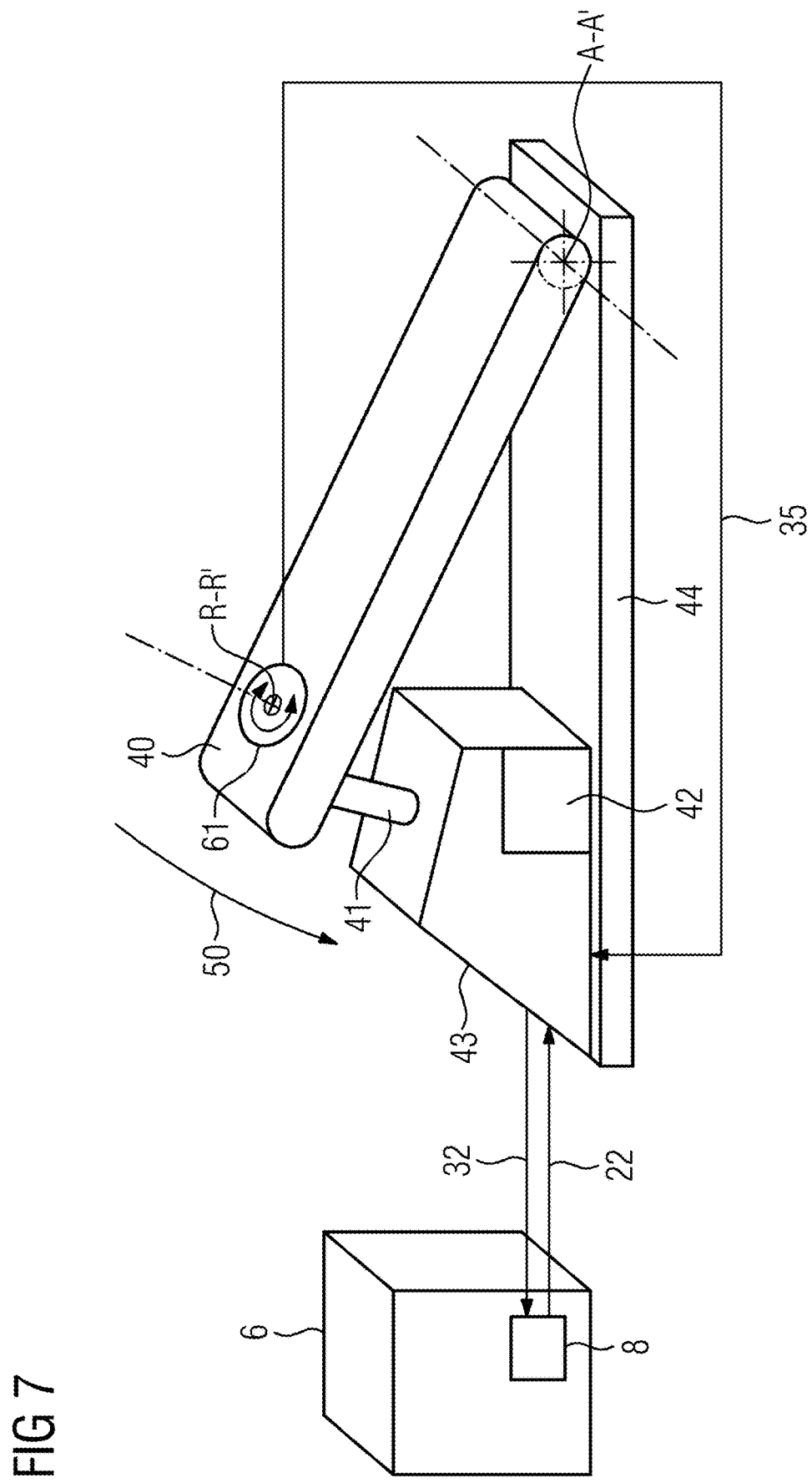
FIG. 7 depicts a schematic diagram of a foot pedal with a turntable unit according to an embodiment.

Depicted in FIG. 7 is a schematic diagram of a perspective view of a foot pedal with a turntable unit. In this advantageous form of embodiment, the turntable unit 61 may include at least one sensor that is embodied to detect a rotational movement of the turntable about the axis R-R'. Through this, a further value of at least one acquisition parameter of the medical x-ray examination, in particular dependent on a deflection direction of the turntable, may be determined. Here, the turntable unit 61 is embodied to send a control command 34 dependent on the deflection direction of the turntable to the lever processing unit 43. The signal unit 42 of the foot pedal may further be embodied, with a deflection of the turntable, to output a signal able to be detected by an operator, in particular dependent on the deflection direction of the turntable.

Figure 8:
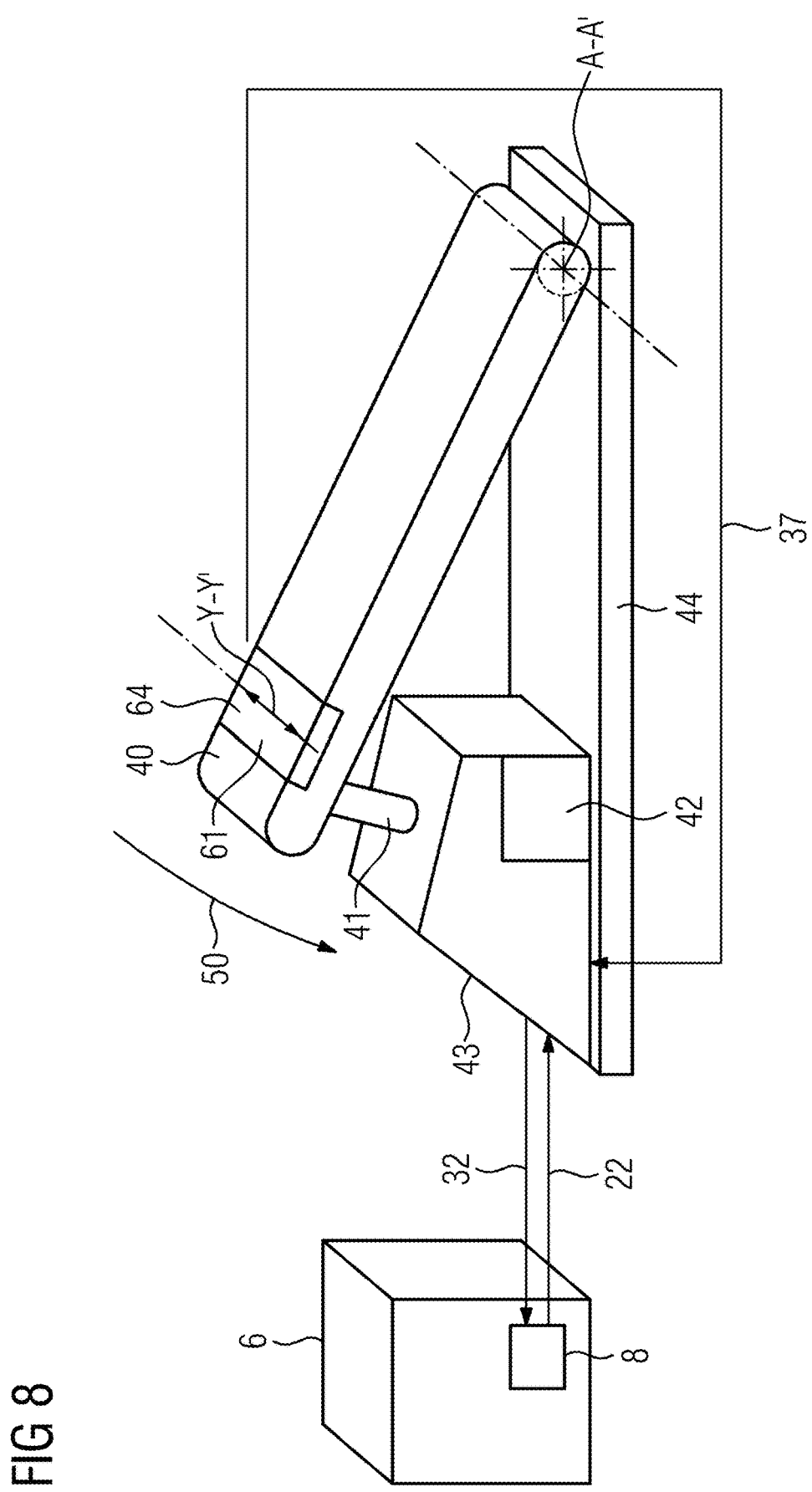
FIG. 8 depicts a schematic diagram of a foot pedal with a shear plate unit according to an embodiment.

Depicted in FIG. 8 is a schematic diagram of a perspective view of a foot pedal with a shear plate unit. In this form of embodiment, the lever arm 40 has a shear plate unit 64, which is arranged on the lever arm 40 and includes a shear plate. In this case, the shear plate unit 64 is embodied to make possible a shear movement of the shear plate along an axis Y-Y' relative to the lever arm 40.

The shear plate unit 64 may further include at least one sensor, which is embodied to detect a shear movement of the shear plate relative to the lever arm 40 and to send a control command 37 to the lever processing unit 43, in particular dependent on a shear movement direction of the shear plate. The lever processing unit 43 then sends a control command 32 to the processing unit 8 whereby a further value of at least one acquisition parameter of the medical x-ray examination may be determined. In particular, the shear plate of the shear plate unit 64 may be supported in such a way that the plate, without any force being applied to it at least partly in one of the shear movement directions by an operator, is located in a rest position and after an end of a corresponding application of a force by the operator, returns to the rest position of its own accord. This may be made possible in particular by springing of the shear plate in the shear plate unit.

Furthermore, the signal unit 42 may be embodied to output a signal able to be detected by an operator on a deflection of the shear plate, in particular dependent on the shear movement direction of the shear plate.

Figure 9:
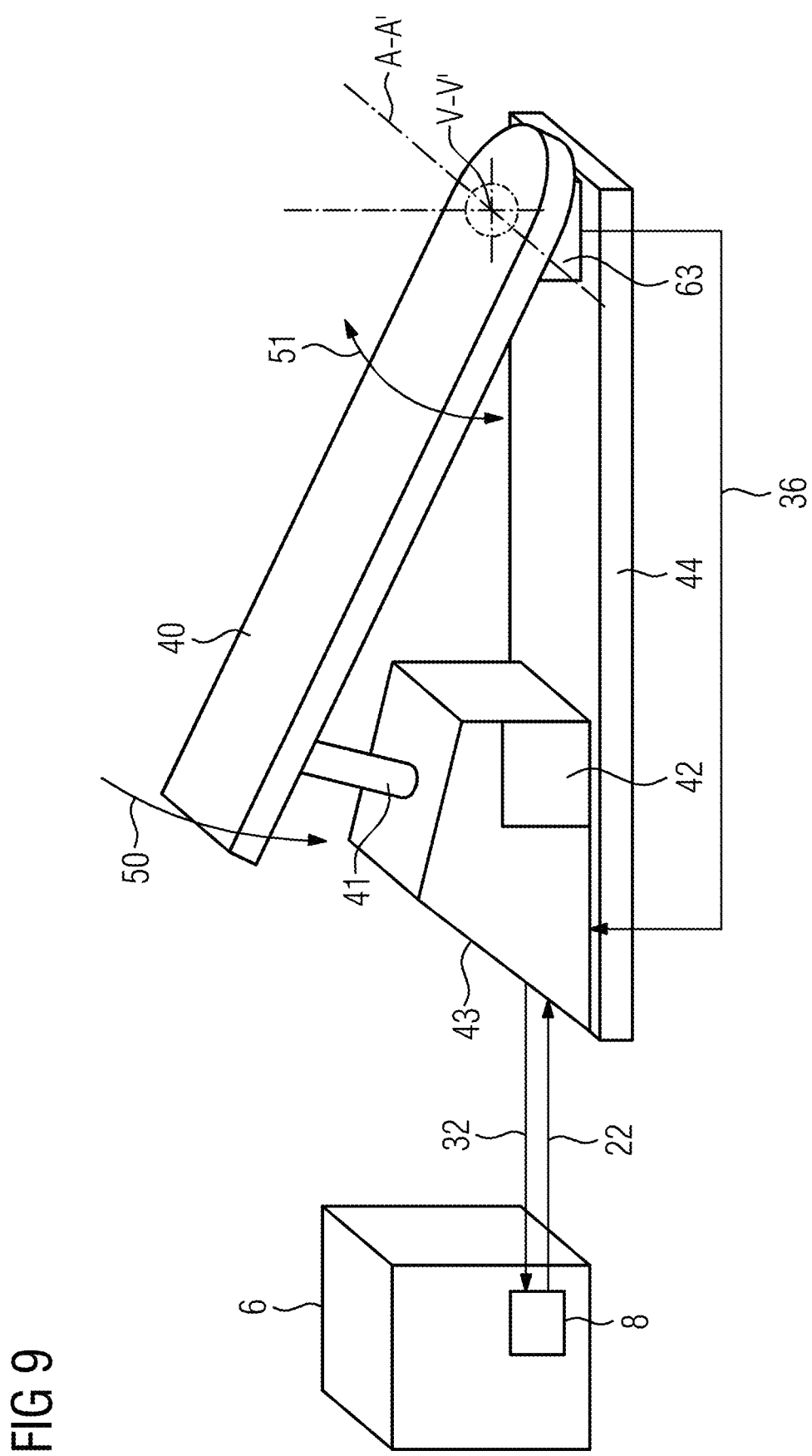
FIG. 9 depicts a schematic diagram of a foot pedal according to an embodiment, wherein the lever arm is able to be deflected about a further axis.

Depicted in FIG. 9 is a schematic diagram of a foot pedal. Here, the lever arm 40 is supported deflectably about a further, in particular vertical, axis V-V', different from the first axis A-A'. In this case, a deflection of the lever arm 40 about the further axis V-V' (e.g., through an end point in each case), in particular a stop point, is restricted in each of the further deflection directions 51. The foot pedal in this form of embodiment further includes a sensor unit 63, which is arranged on the support device of the lever arm 40. The sensor unit 63 may be embodied in particular to send a control command 36 to the lever processing unit 43, in particular dependent on the deflection direction 51 of the lever arm 40. The lever processing unit 43 may then send a control command 32 to the processing unit 8, in particular likewise dependent on the deflection direction of the lever arm about the further axis V-V'.

Furthermore, the sensor unit 63 may be embodied to detect the deflection of the lever arm 40 about the first axis A-A' and about the further axis V-V' independently of one another, for example electronically and/or optically. In this form of embodiment, a plunger 41 would no longer be required to detect the deflection of the lever arm 40 from the rest position RL to the first end point EP1.

The foot pedal may further include a locking unit (not shown), which is embodied to lock at least one deflection direction of the lever arm 40 as a function of a control command 22 from the processing unit 8 of the medical x-ray device 6. Through this, an especially intuitive and blind, in particular sequential, sequence in a selection of an acquisition protocol and a subsequent controlling of a number of acquisition parameters by an operator may be made possible. For example, the deflection direction 50 of the lever arm 40 may be locked by the locking unit until such time as an acquisition protocol has been selected by an operator entry via a deflection of the lever arm in the deflection direction 51. As soon as an acquisition protocol has been selected, the processing unit 8 may send a corresponding control command 22 to the lever processing unit 43, which in its turn sends a control command to the locking unit for release of the deflection direction 50. Through this, a risk of incorrect operation by an operator may be minimized.

In particular, the determination of the further value of at least one acquisition parameter of the medical x-ray examination may trigger storage of the first value, for example, in an acquisition protocol.

The determination of the further value may further make it possible to switch between different recording protocols of the medical x-ray examination, for example, as a function a specific imaging objective, and/or make possible an, in particular sequential, selection of at least one acquisition parameter for the determination of the first value through the deflection of the lever arm 40 from the rest position RL to the first end point EP1. Here, a sequential switchover and/or a sequential selection may be especially intuitive for an operator.

Furthermore, for an adaptation of the determination functions of the lever for determination of the first and/or the second value in each case of at least one acquisition parameter as a function of the acquisition protocol selected at the time, a control command 22 may be sent from the processing unit 8 to the lever unit 7. Through this, for example, with an electromagnetic springing of the lever arm 40, a force resistance, which is directed against the deflection of the lever arm 40, may be tailored adaptively to the acquisition protocol selected at the time.

Depicted in FIG. 10 is a schematic diagram of a hand lever with kick-down stop point. In this form of embodiment, the lever arm 40 may be deflected by a hand entry of an operator from the rest position RL to a first end point EP1 and to a second end point EP2. The first end point EP here is embodied as a kick-down stop point. In this case, a force threshold is arranged at the position of the first end point EP1, which may be overcome by a force of an operator's hand. The hand lever is further embodied in such a way that the lever arm 40, without any force being applied to it by the operator, is located in the rest position RL or returns to the position of its own accord, for example, through springing. It may thus be insured that x-ray scanning of the examination object 1 will not be initiated without an input of an operator by a corresponding force being applied in the deflection direction 50. Furthermore, the second end point EP2 is embodied as a stop point. The hand lever further includes a lever processing unit 43, which is embodied to determine a measure of deflection of the deflection of the lever arm 40 and to send a corresponding control command 32 to the processing unit 8 of the medical x-ray device 6.

The lever arm 40 of the hand lever may further be supported about a further axis (not shown), in particular running along the lever arm 40. Through this, the determination of the further value of at least one acquisition parameter, in particular with a simultaneous deflection of the lever arm in the deflection direction 50, may advantageously be made possible.

Depicted in FIG. 11 is a schematic diagram of the method acts for controlling of acquisition parameters when carrying out a medical x-ray examination. In act S1, by a deflection of the lever arm 40 from the rest position RL, x-ray scanning of the examination object 1 is initiated. Here, in act S2, a first value of at least one acquisition parameter of the medical x-ray examination is determined. In act S3, at least one x-ray image of the examination object 1 is recorded by the medical x-ray device 6 using the first value. With a decision criterion KD, there may further be a check as to whether the lever arm 40 was deflected beyond the kick-down stop point of the first end point EP1 or not. Provided deflection of the lever arm 40 lies between the rest position RL and the first end point, the method explained above is repeated as from act S2. If it is established in decision criterion KD that the lever arm 40 was deflected beyond the first end point EP1 to the second end point EP2, then, in act S4, a second value of at least one acquisition parameter of the medical x-ray examination is determined. In this case, the second value is independent of the measure of deflection of the deflection of the lever arm 40 from the rest position RL to the second end point EP2. Accordingly, the method explained above may be repeated as from act S3, wherein the at least one x-ray image is recorded using the second value.

In conclusion, it is pointed out once again that the method described above in detail as well as the devices shown merely involve exemplary embodiments, which may be modified by the person skilled in the art in a wide diversity of ways without departing from the area of the disclosure. Furthermore, the use of the indefinite article "a" or "an" does not exclude the features concerned also being able to be present multiple times. Likewise, the term "unit" does not exclude the components concerned including a number of interoperating sub-components, which may also be spatially distributed if necessary.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical x-ray device configured to control acquisition parameters when carrying out a medical x-ray examination, the medical x-ray device comprising:
an x-ray unit;
a detection unit;
a lever having a deflectably supported lever arm, wherein the lever arm is configured to be deflected from a rest position to a first end point by a first force provided by an operator, and wherein the lever arm is configured to be deflected to a second end point by a second force provided by the operator that is different from the first force;
a switch; and
a processor configured to:
initiate an x-ray scanning of an examination object by the x-ray unit and the detection unit upon deflection of the lever arm from the rest position,
determine a first value of at least one acquisition parameter of the medical x-ray examination based on the deflection of the lever arm from the rest position to the first end point, wherein the first value is dependent on a measure of deflection by a sensor of the deflection of the lever arm from the rest position to the first end point,
receive a control command from an actuation of the switch by a deflection of lever arm to the second end point, and
determine a second value of the at least one acquisition parameter of the medical x-ray examination using the received control command.

2. The device of claim 1, wherein the first end point is a kick-down stop point.

3. The device of claim 1, wherein the first force and/or the second force is a foot force, a hand force, or a combination thereof.

4. The device of claim 1, wherein the second end point is configured to be reached in a same deflection direction of the lever arm from the rest position as the first end point, and
wherein the second end point is arranged downstream in the deflection direction of the lever arm from the first end point.

5. The device of claim 4, wherein the first end point has a force threshold configured to be overcome by a force,
wherein the second end point is configured to be reached after the force threshold has been overcome by a deflection of the lever arm, and
wherein the second end point is embodied as a stop point.

6. The device of claim 1, wherein the second end point is configured to be reached in another deflection direction of the lever arm from the rest position to the first end point, and
wherein the second end point is arranged in the other deflection direction of the lever arm.

7. The device of claim 1, wherein the switch is arranged such that, on each deflection of the lever arm, the switch is able to be reached by a foot, a hand, or both the foot and the hand of the operator deflecting the lever arm, and
wherein, through the actuation of the switch, a further value of the at least one acquisition parameter of the medical x-ray examination is configured to be determined.

8. The device of claim 1, wherein the lever arm has a turntable unit arranged on the lever arm,
wherein the turntable unit comprises a turntable, and
wherein the turntable unit is configured to make possible a rotational movement of the turntable about an axis at right angles to a support surface of the lever arm.

9. The device of claim 8, wherein the turntable unit comprises at least one sensor configured to detect the rotational movement of the turntable, and
wherein, through the detected rotational movement of the turntable, a further value of the at least one acquisition parameter of the medical x-ray examination, dependent on a deflection direction of the turntable, is configured to be determined.

10. The device of claim 1, wherein the lever arm has a shear plate unit arranged on the lever arm,
wherein the shear plate unit comprises a shear plate, and
wherein the shear plate unit is configured to make possible a shear movement of the shear plate relative to the lever arm.

11. The device of claim 10, wherein the shear plate unit comprises at least one sensor configured to detect the shear movement of the shear plate relative to the lever arm,
wherein, through the detected shear movement of the shear plate, a further value of the at least one acquisition parameter of the medical x-ray examination, dependent on a shear movement direction of the shear plate, is configured to be determined.

12. The device of claim 1, further comprising:
a signal unit configured to output a signal able to be detected by the operator for a deflection of the lever arm, which is determined by the measure of deflection of the lever arm at a time and/or is able to be triggered by the deflection of the lever arm.

13. The device of claim 1, wherein the lever arm is deflected about a first axis,
wherein the lever arm is supported deflectably about a further axis different from the first axis,
wherein a deflection of the lever arm about this further axis is restricted in each case by an end point in each of the further deflection directions, and
wherein a further value of the at least one acquisition parameter of the medical x-ray examination, dependent on a deflection direction of the lever arm about the further axis, is configured to be determined by a deflection of the lever arm about the further axis from the rest position.

14. A medical x-ray apparatus comprising:
a medical x-ray device configured to control acquisition parameters when carrying out a medical x-ray examination, the medical x-ray device having:
an x-ray unit;
a detection unit;
a lever having a deflectably supported lever arm, wherein the lever arm is configured to be deflected from a rest position to a first end point by a first force provided by an operator, and wherein the lever arm is configured to be deflected to a second end point by a second force provided by the operator that is different from the first force;
a switch; and
a processor configured to:
initiate an x-ray scanning of an examination object by the x-ray unit and the detection unit upon deflection of the lever arm from the rest position,
determine a first value of at least one acquisition parameter of the medical x-ray examination based on the deflection of the lever arm from the rest position to the first end point, wherein the first value is dependent on a measure of deflection by a sensor of the deflection of the lever arm from the rest position to the first end point,
receive a control command from an actuation of the switch by a deflection of lever arm to the second end point, and
determine a second value of the at least one acquisition parameter of the medical x-ray examination using the received control command.

15. A method for controlling acquisition parameters when carrying out a medical x-ray examination, the method comprising:
providing a medical x-ray device comprising an x-ray unit, a detection unit, a lever, a switch, and a processor, wherein the lever has a deflectably supported lever arm;
deflecting the lever arm from a rest position to a first end point by a first force provided by an operator and to a second end point by a second force provided by the operator that is different from the first force;
initiating, by the processor of the medical x-ray device, an x-ray scanning of an examination object upon the deflecting of the lever arm from the rest position;
determining, by the processor, a first value of at least one acquisition parameter of the medical x-ray examination based on the deflection of the lever arm from the rest position to the first end point, wherein the first value is dependent on a measure of deflection of the deflection of the lever arm from the rest position to the first end point;
receiving, by the processor, a control command from an actuation of the switch by a deflection of the lever arm to the second end point; and
determining, by the processor, a second value of the at least one acquisition parameter of the medical x-ray examination using the received control command.

16. The method of claim 15, wherein an optimum value of the at least one acquisition parameter of the x-ray examination is determined for the deflection of the lever arm from the rest position to the second end point.

17. The method of claim 15, further comprising:
displaying, on a display unit, a graphical representation of the measure of deflection of the deflection of the lever arm at a time.

18. The method of claim 15, further comprising:
determining, on the actuation of an at least one switch, a further value of the at least one acquisition parameter of the medical x-ray examination.

19. The method of claim 15, further comprising:
determining a further value of the at least one acquisition parameter of the medical x-ray examination, wherein the further value is dependent on a deflection direction of a turntable of the lever arm or a shear movement direction of a shear plate of the lever arm.

20. The method of claim 19, wherein the determination of the further value of the at least one acquisition parameter of the medical x-ray examination triggers storage of the first value in an acquisition protocol.

21. The method of claim 19, wherein the determination of the further value of the at least one acquisition parameter of the medical x-ray examination makes possible a change between different recording protocols of the medical x-ray examination and/or a selection of the at least one acquisition parameter for the determination of the first value of the at least one acquisition parameter by the deflection of the lever arm from the rest position to the first end point.

22. The method of claim 15, wherein an assignment of at least one determination function of the lever for determination of the first value and/or the second value of the at least one acquisition parameter is adapted in each case, and
wherein this adaptation is done as a function of an acquisition protocol of the medical x-ray examination.

23. The method of claim 15, wherein, on the deflection of the lever arm, a signal able to be detected by the operator is output, which is determined by the measure of deflection of the lever arm at a time and/or is triggered by the deflection of the lever arm from the rest position.

\* \* \* \* \*